(12) United States Patent
Augarten

(10) Patent No.: US 8,979,735 B2
(45) Date of Patent: Mar. 17, 2015

(54) CONTROLLER SUPPORT APPARATUS

(71) Applicant: Apollo Endosurgery, Inc., Austin, TX (US)

(72) Inventor: Mike Augarten, Goleta, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 0 days.

(21) Appl. No.: 13/894,799

(22) Filed: May 15, 2013

(65) Prior Publication Data
US 2013/0253261 A1 Sep. 26, 2013

Related U.S. Application Data

(63) Continuation of application No. 12/731,416, filed on Mar. 25, 2010, now abandoned.

(51) Int. Cl.
| A61F 2/00 | (2006.01) |
| A61F 13/00 | (2006.01) |
| A61F 5/00 | (2006.01) |
| F16M 11/04 | (2006.01) |
| F16M 11/06 | (2006.01) |
| F16M 11/18 | (2006.01) |
| F16M 11/20 | (2006.01) |
| F16M 11/24 | (2006.01) |
| F16M 11/42 | (2006.01) |

(52) U.S. Cl.
CPC ............... *A61F 5/0059* (2013.01); *F16M 11/04* (2013.01); *F16M 11/045* (2013.01); *F16M 11/06* (2013.01); *F16M 11/18* (2013.01); *F16M 11/20* (2013.01); *F16M 11/2092* (2013.01); *F16M 11/24* (2013.01); *F16M 11/42* (2013.01); *F16M 2200/063* (2013.01)

USPC ............. 600/37; 128/897; 128/898; 128/899; 108/137; 108/138; 108/143; 108/144.11; 108/147.19; 248/122.1

(58) Field of Classification Search
CPC .... A61F 5/0059; F16M 11/04; F16M 11/045; F16M 11/06; F16M 2200/063; F16M 11/20; F16M 11/2092; F16M 11/24; F16M 11/42; F16M 11/18
USPC .................. 600/37; 248/122.1; 108/137, 138, 108/144.11, 147.19, 143; 128/897–899
See application file for complete search history.

(56) References Cited

U.S. PATENT DOCUMENTS

| 5,597,146 A * | 1/1997 | Putman ....................... 248/276.1 |
| 6,459,924 B1 * | 10/2002 | Creighton et al. ............. 600/427 |
| 6,565,410 B1 * | 5/2003 | Allen ............................ 446/454 |
| 7,189,249 B2 | 3/2007 | Hart |

(Continued)

*Primary Examiner* — Christine H Matthews
*Assistant Examiner* — Sunita Reddy
(74) *Attorney, Agent, or Firm* — Gordon & Jacobson, PC

(57) ABSTRACT

An apparatus comprises a controller for remotely controlling an implantable device that is used to adjust a gastric band, and the controller transmits a telemetric signal to the implantable device. The apparatus further comprises a table that provides support for the controller. A rail is oriented in a first direction with respect to the table, and a tray is slidably coupled to the rail. The tray receives the controller, and the rail moves the tray and the controller in the first direction with respect to the table. The apparatus further comprises a roller coupled to the rail. The roller aids in moving the rail, the tray, and the controller in a second direction with respect to the table. The apparatus further comprises an attachment mechanism for securing the controller to the tray. The apparatus locates the controller in a desired location with respect to a patient.

8 Claims, 3 Drawing Sheets

(56) References Cited

U.S. PATENT DOCUMENTS

| | | |
|---|---|---|
| 7,286,881 B2 | 10/2007 | Schommer |
| 8,678,993 B2 | 3/2014 | Stroumpoulis |
| 2002/0148394 A1* | 10/2002 | Strong .................... 108/147.21 |
| 2003/0115671 A1* | 6/2003 | Smeed ........................... 5/503.1 |
| 2004/0172012 A1* | 9/2004 | Otsuka et al. .................... 606/1 |
| 2006/0161039 A1* | 7/2006 | Juliana et al. ..................... 600/9 |
| 2007/0156013 A1* | 7/2007 | Birk ................................ 600/37 |
| 2008/0222813 A1 | 9/2008 | Aikman |
| 2008/0272251 A1 | 11/2008 | Brown |
| 2010/0080360 A1* | 4/2010 | Ohta et al. ..................... 378/209 |
| 2010/0107320 A1* | 5/2010 | Rees ............................... 2/456 |
| 2011/0201874 A1 | 8/2011 | Birk |
| 2011/0201875 A1 | 8/2011 | Stroumpoulis |

\* cited by examiner

CONTROLLER SUPPORT APPARATUS

CROSS REFERENCE TO RELATED APPLICATIONS

This application is a continuation of U.S. patent application Ser. No. 12/731,416, filed Mar. 25, 2010, the contents of which is incorporated herein by reference.

FIELD

The present description generally relates to medical systems and apparatus and uses thereof for treating obesity and/or obesity-related diseases, and more specifically, relates to support apparatus used for remotely adjustable gastric band controllers.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts food's passage into a lower portion of the stomach. When the stoma is of an appropriate size that is restricted by a gastric band, food held in the upper portion of the stomach provides a feeling of satiety or fullness that discourages overeating. Unlike gastric bypass procedures, gastric band apparatus are reversible and require no permanent modification to the gastrointestinal tract.

Over time, a stoma created by a gastric band may need adjustment in order to maintain an appropriate size, which is neither too restrictive nor too passive. Accordingly, prior art gastric band systems provide a subcutaneous fluid access port connected to an expandable or inflatable portion of the gastric band. By adding fluid to or removing fluid from the inflatable portion, the effective size of the gastric band can be adjusted to provide a tighter or looser constriction.

Some remotely adjustable gastric banding systems have been proposed that utilize a controller to non-invasively fill and drain the gastric band. For example, internal pumps may be utilized to fill and drain the gastric band, and these internal pumps may be controlled telemetrically by an external controller. The controller may be used to send radio frequency waves for powering and communicating with the implanted device. The implanted device can fill or drain the gastric band as requested by the healthcare worker via the handheld controller. Such remotely adjustable gastric bands have been described in Birk et al., U.S. patent application Ser. No. 12/705,245 (published as U.S. Patent Application Publication No. 2011/0201874), and Stroumpoulis, U.S. patent application Ser. No. 12/705,343 (published as U.S. Patent Application Publication No. 2011/0201875), the entire disclosures of which are incorporated herein by this specific reference.

Controllers for remotely adjustable gastric banding systems may be of a size and weight that cause manipulation of these controllers to be difficult. For example, the controller can weigh more than a couple of pounds and adjustments by hand can take several minutes. Holding the controller in the desired position for the desired time may also be difficult. Further, the accurate positioning of the controller is important in order to facilitate appropriate communication with the gastric banding system.

Some devices exist that facilitate manipulation of objects. For example, Aikman, U.S. Patent Application Pub. No. 2008/0222813, is directed toward a system for positioning a patient on a bed to encourage side sleeping. The system comprises a rigid, but flexible pillow that is fixed with respect to the patient. This publication does not address a method or system for positioning an object with respect to a patient; rather, it discloses positioning a patient with respect to an object. Furthermore, the positioning required in Aikman may not be conducive to utilizing a remotely adjustable gastric banding system controller.

Otsuka, et al., U.S. Pat. No. 7,189,246, generally discloses a medical instrument holding device that allows manipulation of a medical instrument. One end of an arm of the holding device is attached to a rail which allows for movement of the base of the device in one dimension. Thus it is desirable to develop a support system for a controller that is capable of more mobile and less-restrained positioning of the controller.

Schommer, et al., U.S. Pat. No. 7,286,881, discloses an external power source, and system and method using such external power source, for an implantable medical device having therapeutic componentry and a secondary coil operatively coupled to the therapeutic componentry. A belt is used to position the external power source near the patient, and devices of only limited weight may be positioned with this belt. Thus, it is desirable to develop a positioning and support system that can provide support for heavier devices and that may facilitate easier, more flexible positioning of a gastric banding system controller.

Brown, et al., U.S. Patent Application Pub. No. 2008/0272251, discloses a holding device for medical purposes having a carrier arm on whose distal end a medical instrument can be secured and having at least one joint for positioning the carrier arm and/or the medical instrument. But Brown's device is utilized for devices of limited size and weight, and Brown is limited to certain types of movement.

As noted, these devices suffer from certain disadvantages. For example, the devices are not designed for the size and weight of a controller for a remotely adjustable gastric banding system. Further, these devices do not provide for desired flexibility in positioning such controllers. Moreover, these devices do not allow for adequate positioning and maintenance of the controller in a desired location.

Thus, a need exists for a support apparatus for a remotely adjustable gastric banding system controller that allows a physician to more easily and accurately position the controller with respect to the patient and maintain the controller in that position during an adjustment of the gastric band.

SUMMARY

Generally described herein are support apparatus for controllers used in remotely adjustable gastric banding systems. The apparatus and methods described herein aid in facilitating obesity control and/or treating obesity-related diseases.

In one embodiment, an apparatus comprises a controller for remotely controlling an implantable device that is used to adjust a gastric band, and the controller transmits a telemetric signal to the implantable device. The apparatus further comprises a table that provides support for the controller. A rail is oriented in a first direction with respect to the table, and a tray is slidably coupled to the rail. The tray receives the controller, and the rail moves the tray and the controller in the first direction with respect to the table.

The apparatus further comprises a roller coupled to the rail. The roller aids in moving the rail, the tray, and the controller in a second direction with respect to the table. In an embodiment, the apparatus further comprises an attachment mechanism for securing the controller to the tray. The attachment mechanism may be a strap, a cup, a cavity, a tray, a grasper, and combinations thereof.

Additionally, the apparatus may comprise an adjustable leg that is movable with respect to the table. The adjustable leg may be used to adjust a height of the table to accommodate various patient sizes. The adjustable leg comprises a telescoping pole that helps move the adjustable leg with respect to the table. A knob may be used to lock the telescoping pole and the leg in place.

In accordance with another embodiment of the present invention, an apparatus comprises a base and a fixed pole connected to the base. A manipulator is connected to the fixed pole at a first end of the manipulator arm. The manipulator arm is capable of moving while the fixed pole is stationary.

The apparatus further comprises an attachment device, coupled to a second end of the manipulator arm. A controller is coupled to the manipulator arm via the attachment device, and the controller remotely controls an implantable device that is used to adjust a gastric band. The controller transmits a telemetric signal to the implantable device in order to adjust the gastric band.

In an embodiment, the apparatus comprises a plurality of wheels attached to the base. The wheels allow an operator to move the fixed pole. At least one of the plurality of wheels comprises a brake or a lock so the operator may lock the apparatus in a desired location.

Further, in accordance with an embodiment, the manipulator arm comprises a first movable segment and a second movable segment. A first friction stop swivel joint connects the first movable segment to the second movable segment, and the first friction stop swivel joint maintains a position of the controller when the controller weighs from approximately three pounds to approximately eight pounds. The first friction stop swivel joint may comprise a knob to lock the first friction stop swivel joint.

Other embodiments of the present invention include a second friction stop swivel joint connecting the second movable segment to a third movable segment. The first friction stop swivel joint rotates about a first axis, and the second friction stop swivel joint rotates about a second axis different than the first axis. These different axes allow three-dimensional movement of the controller.

In accordance with an embodiment, a method for positioning a controller of a remotely adjustable gastric banding system near a patient comprises positioning the controller proximate a support apparatus. The controller is attached to the support apparatus using an attachment mechanism. The attachment mechanism may be one or more of the following: a strap, a cup, a cavity, a tray, a grasper, and combinations thereof. The support apparatus is adjusted to move the controller to a position for remotely adjusting an implantable gastric band. The support apparatus may be adjusted without an operator holding the controller.

In a further embodiment, the method also comprises adjusting a telescoping pole to increase or decrease a height of the support apparatus. The telescoping pole may then be locked in place. The controller may be positioned on a tray, and an operator may slide the tray and the controller in a first direction. The operator may also slide the tray and the controller in a second direction to appropriately position the controller with respect to the patient.

In another embodiment, the method comprises moving a manipulator arm to appropriately position the controller with respect to the patient. A friction stop swivel joint coupled to the manipulator arm may be locked to prevent undesired movement of the controller.

DETAILED DESCRIPTION

The present invention generally provides a support apparatus used for remotely adjustable gastric band controllers.

In accordance with various embodiments, the support apparatus described herein provide flexible and stabilizing support for hand-held gastric banding system controllers. Such flexible and stabilizing support may be provided during adjustments to the gastric banding system to facilitate reducing errors related to drift and/or motion of the controller and to reduce errors due to fatigue of the operator and/or the patient.

The controllers disclosed herein communicate telemetrically with and provide access to gastric banding system data and functions and are external, handheld, reusable battery-powered devices that are generally cylindrical in shape. The controller has a user interface including at least one display and at least one user input. The controller permits a clinician or a patient to navigate through menu driven screens used for data entry, data collection, and control of the gastric banding system. The controllers disclosed herein may weigh between approximately three pounds and approximately eight pounds.

The controller is capable of communicating with the gastric banding system. "Capable of communicating" as used herein refers to the remote transmitter's ability to establish communications with the gastric banding system, yet still have the ability to break communication and the systems described herein still function. For example, the controller may communicate using radio frequency or other frequency wavelengths or telemetric signals.

To establish communication, in one example embodiment, once the controller is initialized, a display shows a searching query for a nearby gastric banding system. As the controller is brought within a range of the gastric banding system, the display shows the strength of the communication link. Once stable communications have been acquired, the display shows the serial number of the system so a clinician can verify they have the appropriate patient records in hand. If the patient requires a tightening of the gastric band, the clinician can enter the amount of the desired volume increase for the gastric band. The controller can also display the current volume within the gastric band and indicate the new volume as the gastric band fills. The controller can also indicate desired and actual volumes during draining of the gastric band. As such, various embodiments of the present invention provide apparatus for maintaining the controller in a desired position for a period of time to accomplish the above and other tasks.

Figure 1:
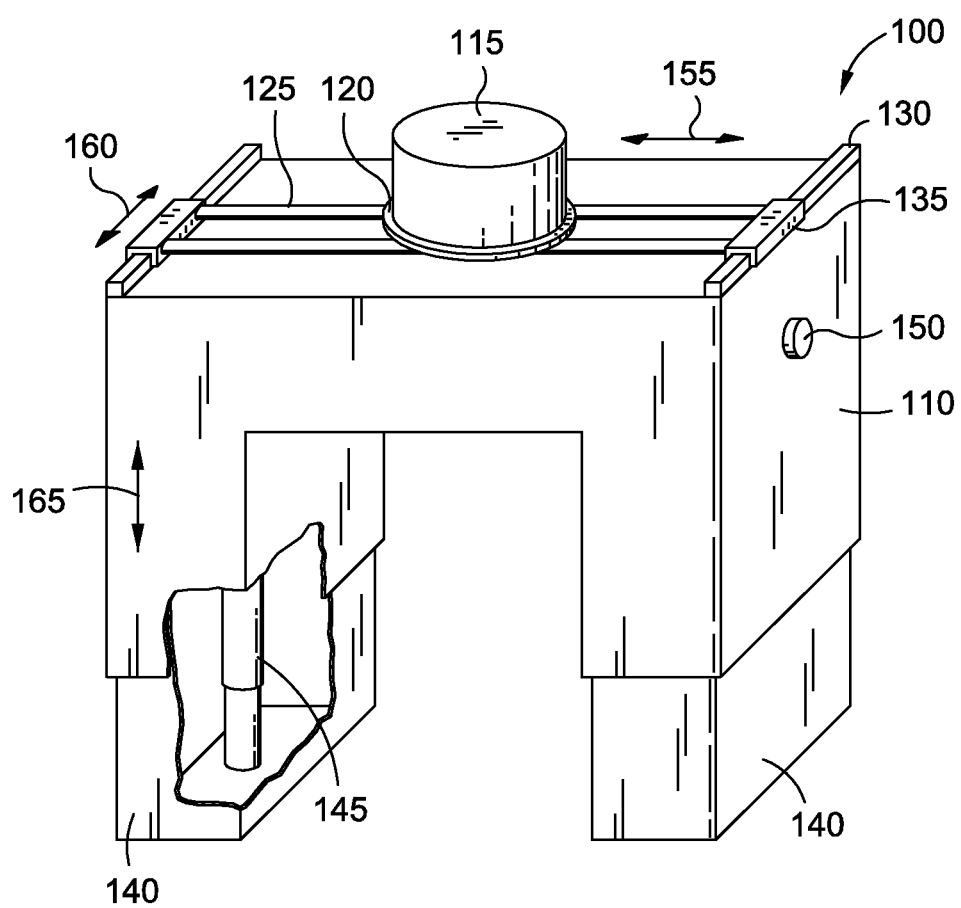
FIG. 1 illustrates a perspective, cut-away view of a support apparatus for a gastric banding system controller according to an embodiment of the present invention.

Turning now to FIG. 1, in an embodiment of the present invention, a support apparatus 100 comprises a table 110 having a tray 120 that provides support and positioning for a controller 115, such as a controller for a gastric banding system. The controller 115 may be referred to as a "handheld" controller because the controller 115 may typically be held in a patient's or physician's hand where the support apparatus 100 is not being used.

In an embodiment, the tray 120 is specifically designed for the controller 115 that is used in connection with a remotely-adjustable gastric banding system. The form, fit and function of the tray 120 are advantageously designed to provide support to and manipulation of the controller 115. For example, the tray 120 is a similar shape as the controller 115, and the tray 120 may have precisely aligned securing features, as discussed further below.

The tray 120 may be slidably connected to a rail 125 or set of rails 125 to facilitate moving the tray 120 in a first direction 155 with respect to a surface of the table 110. Moving the tray 120 in the first direction 155 facilitates positioning the controller 115 in a location with respect to the patient that allows the controller 115 to communicate with the gastric banding system.

The rail 125 may interface with the tray 120 in any manner known in the art that allows the tray 120 to slide with respect to the rail 125. The tray 120 and/or the rail 125 may comprise roller bearings or other bearing types to allow the tray 120 to slide with respect to the rail 125. In an embodiment, the tray 120 and the rail 125 may comprise bearing and/or contact surfaces with a coefficient of friction sufficient to allow movement of the tray 120 and to keep the tray 120 in a given position determined by the physician, operator, and/or the patient. In an embodiment, the degree of friction between the tray 120 and the rail 125 is sufficient to restrict movement of the tray 120 unless the tray 120 is purposely repositioned by an operator.

In various embodiments, the support apparatus 100 is designed to securely fit and/or maintain the controller 115 in place while allowing it to have motion within a plane when moved by an operator. For example, an attachment mechanism such as a strap, a cup, a cavity, a tray, a grasper, and combinations thereof may be used to secure the controller 115 to the tray 120. The tray 120 may be advantageously designed to secure the controller 115 in place using the attachment mechanism. Furthermore, the controller 115 may comprise attachment locations for receiving the attachment mechanism, such as loops or grooves for a strap.

The tray 120 can move side-to-side in the first direction 155 by sliding on the rail 125 as discussed above. The tray 120 may move in a second direction 160 with a motion substantially perpendicular to the motion of the rail 125 in the first direction 155.

In an embodiment, a second set of rails and/or guides 130 may be located on each side of the table 110. The guides 130 may allow the rails 125 themselves to move in the second direction 160 with respect to the table 110. In an embodiment, rollers 135 at the end of the rails 125 may include a bearing or other device that interacts with the guides 130 to guide the motion of the rails 125. In further embodiments, any device may be employed that allows movement of the tray 120 in the second direction 160. A sufficient amount of friction may exist between the rollers 135 and the guides 130 such that the tray 120 may remain in place if the controller 115 is not being purposely moved by an operator.

Figure 2:
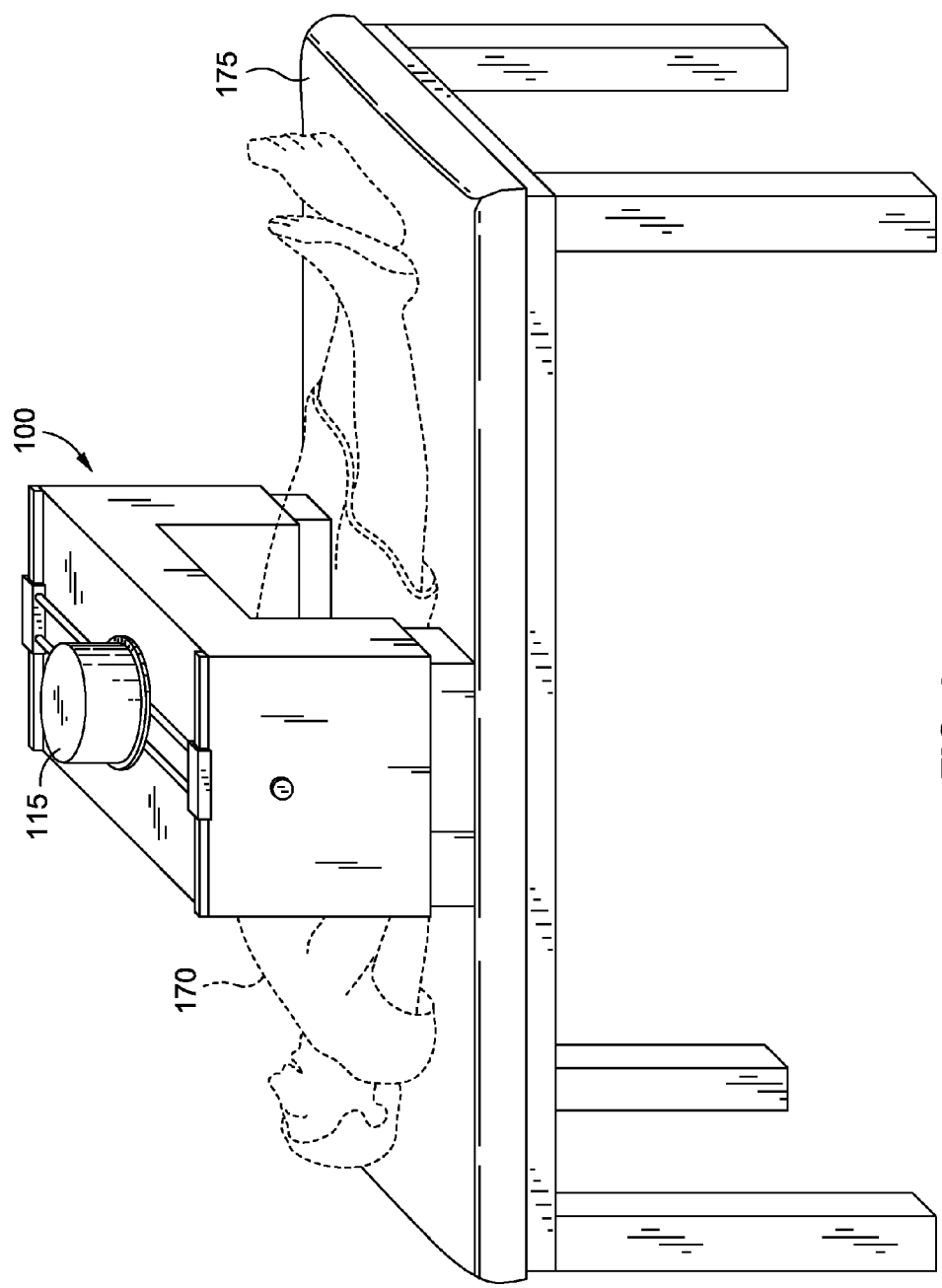
FIG. 2 illustrates a perspective view of a support apparatus positioned with respect to a patient according to an embodiment.

With reference to FIG. 2, according to an embodiment of the present invention, the support apparatus 100 is configured to accommodate a patient 170 on an examination table 175. Because the support apparatus 100 may be utilized for patients of various sizes, embodiments of the present invention, with reference again to FIG. 1, comprise adjustable legs 140. The legs 140 and/or table 110 may move in a height adjustment direction 165 to add flexibility to the support apparatus 100 and to accommodate various sizes of patients.

Movement of the table 110 and/or the legs 140 may be accomplished with a telescoping pole 145 coupled to the legs 140. In an embodiment, the legs 140 may slide within the table 110 to facilitate adjusting the height, and the telescoping pole 145 may be disposed within one or both of the legs 140. In another embodiment, the telescoping pole 145 may extend out the bottom of the table 110 and may have feet that contact the floor and/or the examination table.

An operator may move the table 110 and/or the legs 140 to increase or decrease the height of the support apparatus 100. As the height of the support apparatus 100 increases, the telescoping pole 145 expands, and as the height of the support apparatus 100 decreases, the telescoping pole 145 contracts. The operator may secure the support apparatus 100 at the desired height by turning a knob 150 on each side of the support apparatus 100. Turning the knob 150 applies friction to the telescoping pole 145 to maintain the desired height of the support apparatus 100. Other mechanisms can be used to maintain the desired height such as a detent in leg mechanism or a peg and hole mechanism.

In an embodiment, the various components of support apparatus 100 are constructed of non-metallic materials so as not to interfere with the radio frequency functionality of the controller 115 and inductive operations of the gastric banding system.

With the support apparatus 100 at the desired height, the operator may slide the controller 115 and/or the tray 120 in the first direction and/or the second direction to a location appropriate for remotely adjusting the gastric banding system. Once the controller 115 is in the appropriate location, adjustments to and/or readings from the gastric banding system may be made while the support apparatus 100 prevents drift and/or motion of the controller and prevents fatigue of the operator and/or the patient who might otherwise hold the controller in his hand.

Figure 3:
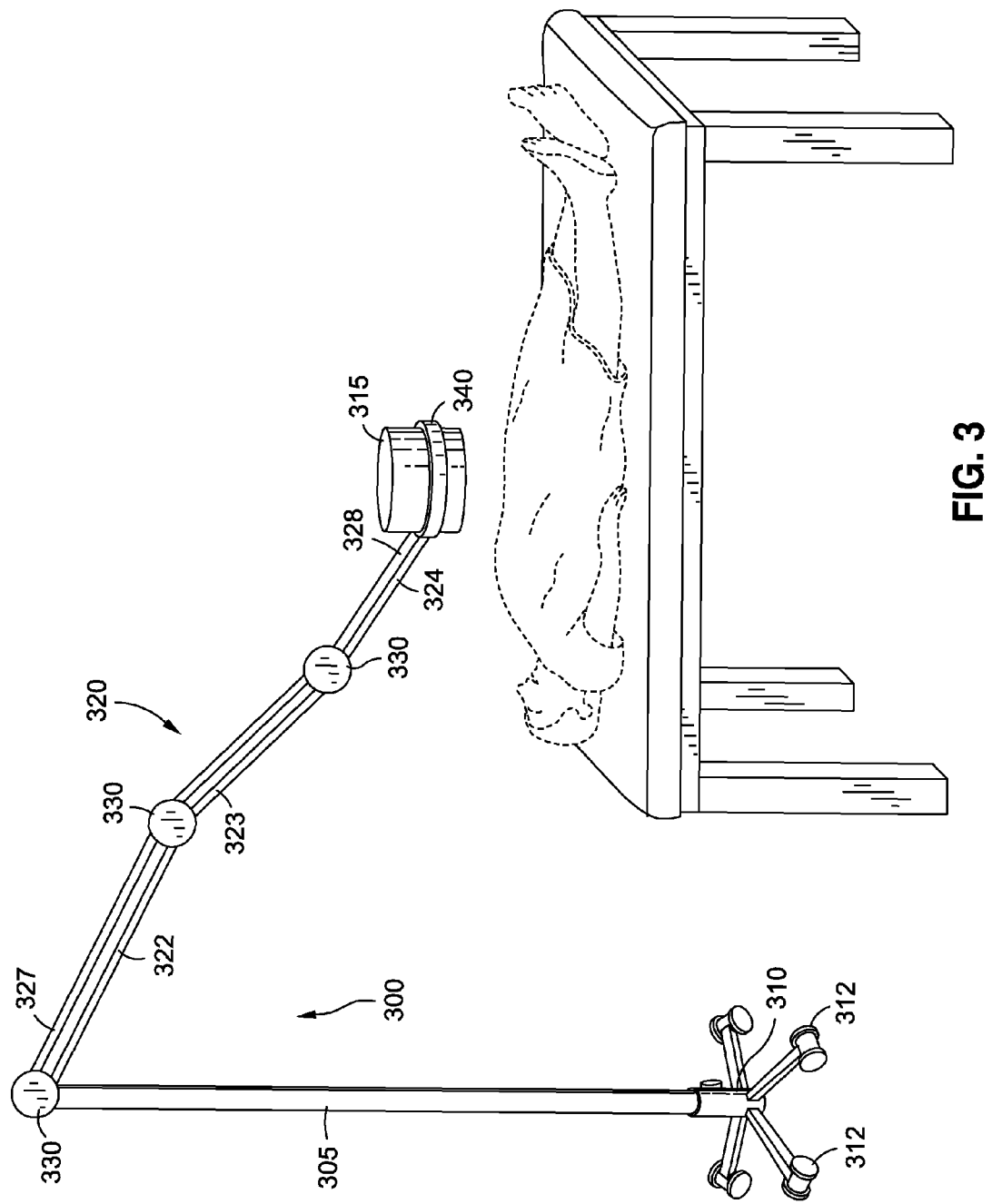
FIG. 3 illustrates a perspective view of a support apparatus for a gastric banding system controller according to another embodiment of the present invention.

Turning now to FIG. 3, in an embodiment, a support apparatus 300 for a controller 315 comprises a movable pole, such as a manipulator arm 320. The manipulator arm 320 allows an operator to move the controller 315 to a desired position with respect to a patient. As noted above, the controller 315 may be used to make remote adjustments to a gastric banding system located within a patient's body. The support apparatus 300 facilitates maintaining controller 315 in a desired position for a certain time while reducing errors related to drift and/or motion of the controller and related to fatigue of the operator and/or the patient.

The support apparatus 300 comprises a base 310. The base 310 may be weighted to prevent the support apparatus 300 from toppling and/or moving when the controller 315 is secured to the support apparatus 300. For example, the base 310 may be advantageously designed to counter-balance the weight of the controller 315, where the controller 315 weighs between approximately three pounds and approximately eight pounds.

The base 310 further comprises wheels 312 so that an operator may move the support apparatus 300 to a desired location close to a patient. The wheels 312 are configured to provide sufficient resistance to rolling such that the support apparatus 300 will not move unless moved by an operator. For example, the wheels 312 may have a small amount of friction, or the wheels 312 may comprise a wheel brake to prevent unwanted rolling of the support apparatus 300.

A fixed pole 305 is connected to and extends vertically from the base 310 to allow the controller 315 to be placed above a patient, either in a prone position or in any inclined position. The manipulator arm 320 has a first end 327 that is coupled to the fixed pole 305, and the manipulator arm 320 may move independently of the fixed pole 305. In other words, the manipulator arm 320 may move while the fixed pole 305 remains stationary. A second end 328 of the manipulator arm 320 is coupled to an attachment mechanism 340 that secures the controller 315 to the support apparatus 300.

The attachment mechanism 340 may comprise a support mechanism, such as a plate or a tray, and/or a holder including one or more of the following: a strap, a cup, a cavity, a tray, a grasper, and combinations thereof. In an embodiment, the attachment mechanism 340 comprises a strap that secures the controller 315 to the second end 328 of the manipulator arm 320. In another embodiment, the attachment mechanism 340 may comprise a tray secured to the manipulator arm 320, and the controller 315 may sit on the tray. A strap may then be configured to secure the controller 315 to the tray. The strap and/or other attachment mechanism may be advantageously sized for the controller 315, and the controller 315 may have specific connection points for the strap.

Various components near the controller 315, such as the attachment mechanism 340 and the manipulator arm 320 near the second end 328 of the manipulator arm 320, may be made of a non-metallic material so as to not interfere with the operation of the controller 315.

Utilizing the attachment mechanism 340 in conjunction with the support apparatus 300 allows the controller 315 to become a "hands-free" controller. Typically, the controller 315 would be a "hand-held" controller because an operator, physician, and/or patient would need to hold the controller 315 by hand in order to perform adjustments to the gastric banding system. However, attachment mechanism 340 allows the controller 315 to more accurately be positioned without being held by an operator.

In an embodiment, the manipulator arm 320 comprises movable segments 322, 323, 324. These movable segments 322, 323, 324 allow for finer positioning of the controller 315. The movable segments 322, 323, 324 may be connected to each other using friction stop swivel joints 330. Friction stop swivel joints may also be used to connect the manipulator arm 320 to the fixed pole 305 and/or the attachment mechanism 340.

The swivel joints 330 are configured to have sufficient friction such that the movable segments 322, 323, 324 stay in place unless an operator desires them to move. In an embodiment, each swivel joint 330 may comprise a locking mechanism, such as a knob, that restricts movement of the swivel joint 330 if the locking mechanism is engaged.

In an embodiment, the swivel joints 330 allow motion about one axis and/or in one plane. In another embodiment, the swivel joints 330 may move about multiple axes and/or in multiple planes. It should be understood that any combination of single/multiple axes/plane swivel joints 330 may be used without departing from the scope of the present invention. Various combinations of the swivel joints 330 allow for three dimensional movements and positioning of the controller 315. Further, using various combinations of the swivel joints 330 allows a compromise between positioning flexibility and cost and complexity of the support apparatus 300.

In accordance with various embodiments, the support apparatus 100, 300 may include electromechanical devices to facilitate automated, hands-free operation of the support apparatus 100, 300. Height and/or positional adjustments may then be made via motors, servos, gears, and the like to appropriately locate the controller 115, 315 to perform adjustments to the gastric banding system. Computers may be utilized for precise positioning control.

According to an embodiment, a method for positioning a controller of a remotely adjustable gastric banding system comprises securing the controller to a support apparatus. The controller may be secured to the support apparatus using an attachment mechanism including one or more of the following: a strap, a cup, a cavity, a tray, a grasper, and combinations thereof. An operator may adjust the position of the controller with respect to the support apparatus without the operator holding the controller.

In an embodiment, as illustrated in FIG. 1, the support apparatus 100 is adjusted to accommodate a patient. The adjustable legs 140 are adjusted by causing the telescoping pole 145 to expand or collapse. The adjustable legs 140 may be locked in place using the knob 150. The adjustable legs 140 may be adjusted, and other adjustments to the support apparatus 100 may be made before and/or after securing the controller 115 to the support apparatus 100. Similarly, the tray 120 may be moved in the first direction 155 and/or the second direction 160 before and/or after securing the controller 115 to the tray 120.

In an embodiment, as illustrated in FIG. 3, the support apparatus 300 may be rolled towards a patient before and/or after securing the controller 315 to the attachment mechanism 340. The manipulator arm 320 is then moved with respect to the fixed pole 305 to position the controller 315 in a desired location for adjusting the gastric band. The support apparatus 300 may be positioned near the patient, and other adjustments to the support apparatus 300 may be made before and/or after securing the controller 315 to the support apparatus 300 and/or the attachment mechanism 340.

Embodiments of the present invention provide advantages over the prior art. Although many other advantages will be apparent, some are discussed here. For example, the support apparatus disclosed herein remove the requirement for an operator to hold the gastric banding system controller during adjustment of the gastric band. Because of the positioning requirements for successful operation of the controller and adjustment of the gastric band, this hands-free system is more user-friendly and accurate, and does not lead to operator fatigue. Further, the patient, physician, and/or operator may perform certain other tasks during adjustment of the gastric band because their hands are free to do so.

Unless otherwise indicated, all numbers expressing weights, sizes and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An apparatus comprising:
   a controller that remotely controls an implantable device that is used to adjust a gastric band, the controller transmitting a telemetric signal to the implantable device;
   a table for providing support for the controller;
   a rail oriented in a first direction with respect to the table;
   a tray slidably coupled to the rail for receiving the controller and moving the tray and the controller in the first direction with respect to the table;
   a roller coupled to the rail for moving the rail, the tray, and the controller in a second direction, substantially perpendicular to the first direction, with respect to the table; and
   an adjustable leg extending longitudinally along an axis, the leg being adjustable with respect to the table for adjusting a height of the table, wherein the adjustable leg comprises a plurality of tubular poles each arranged one inside another for telescoping movement along the longitudinal axis, wherein all of the tubular poles are coaxially aligned with the longitudinal axis.

2. The apparatus of claim 1 further comprising a non-metallic attachment mechanism for securing the controller to the tray.

3. The apparatus of claim 2 wherein the non-metallic attachment mechanism is selected from a group consisting of a strap, a cup, a cavity, a tray, a grasper, and combinations thereof.

4. The apparatus of claim 1 further comprising a knob operatively coupled to the tubular poles for maintaining the height of the table.

5. The apparatus of claim 1 wherein the tubular poles are within the adjustable leg.

6. The apparatus of claim 1 wherein the adjustable leg comprises a foot coupled to the tubular poles.

7. The apparatus of claim 1 wherein the controller weighs approximately three pounds to approximately eight pounds, and wherein the tray is capable of moving and maintaining position of the controller.

8. The apparatus of claim 1 further comprising an electromechanical device for automatic movement of the tray or the rail.

* * * * *